(12) United States Patent
Forsberg et al.

(10) Patent No.: US 7,551,960 B2
(45) Date of Patent: Jun. 23, 2009

(54) EXTERNAL PRESENTATION OF ELECTRICAL STIMULATION PARAMETERS

(75) Inventors: John W. Forsberg, St. Paul, MN (US); Jeffry C. Palm, Coon Rapids, MN (US); Mark G. Wosmek, Ramsey, MN (US); Steven T. Deininger, Savage, MN (US); Raymond F. McMullen, Shorewood, MN (US); Matthew J. Michaels, Glendale, AZ (US); Kevin J. Kelly, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 561 days.

(21) Appl. No.: 11/222,501

(22) Filed: Sep. 8, 2005

(65) Prior Publication Data

US 2007/0055318 A1 Mar. 8, 2007

(51) Int. Cl.
*A61N 1/08* (2006.01)
(52) U.S. Cl. .............................. 607/7; 607/11; 607/27; 607/59; 607/61; 607/117; 607/116; 600/523; 600/554
(58) Field of Classification Search .................. 607/7, 607/11, 2, 8, 27, 45, 46, 52, 59, 61; 600/523, 600/554; 434/262
See application file for complete search history.

(56) References Cited

U.S. PATENT DOCUMENTS

| | | | |
|---|---|---|---|
| 4,141,367 A | 2/1979 | Ferreira | |
| 4,236,524 A | 12/1980 | Powell et al. | |
| 4,638,436 A * | 1/1987 | Badger et al. | 607/102 |
| 5,036,850 A | 8/1991 | Owens | |
| 5,123,413 A | 6/1992 | Hasegawa et al. | |
| 5,183,041 A * | 2/1993 | Toriu et al. | 607/46 |
| 5,243,975 A | 9/1993 | Alferness et al. | |
| 5,300,096 A | 4/1994 | Hall et al. | |
| 5,342,403 A | 8/1994 | Powers et al. | |
| 5,370,672 A | 12/1994 | Fowler et al. | |
| 5,578,060 A | 11/1996 | Pohl et al. | |
| 5,893,883 A | 4/1999 | Torgerson et al. | |
| 5,938,690 A | 8/1999 | Law et al. | |
| 6,308,102 B1 | 10/2001 | Sieracki et al. | |

(Continued)

FOREIGN PATENT DOCUMENTS

WO WO 97/49455 12/1997

(Continued)

OTHER PUBLICATIONS

Response to Office Action dated Nov. 12, 2007 for U.S. Appl. No. 11/222,495 (26 pgs.).

(Continued)

*Primary Examiner*—Carl H Layno
*Assistant Examiner*—Natasha N Patel
(74) *Attorney, Agent, or Firm*—Shumaker & Sieffert, P.A.

(57) ABSTRACT

An external indicator device presents parameters associated with stimulation therapy generated by a pulse generator, which may be associated with an external or implantable stimulation device. In this manner, the external indicator device enables a user to visualize stimulation parameters without actually delivering stimulation therapy to a patient via implanted electrodes. The electrical stimulation parameters may include electrical amplitude levels, pulse widths, pulse rates, electrode combinations, and electrode polarities for stimulation generated by the pulse generator.

40 Claims, 9 Drawing Sheets

U.S. PATENT DOCUMENTS

| | | | |
|---|---|---|---|
| 6,516,227 B1 * | 2/2003 | Meadows et al. | 607/46 |
| 6,580,948 B2 | 6/2003 | Haupert et al. | |
| 6,609,032 B1 | 8/2003 | Woods et al. | |
| 6,622,048 B1 | 9/2003 | Mann et al. | |
| 6,654,642 B2 | 11/2003 | North et al. | |
| 6,687,538 B1 | 2/2004 | Hrdlicka et al. | |
| 6,907,287 B1 | 6/2005 | Bevan et al. | |
| 6,978,171 B2 | 12/2005 | Goetz et al. | |
| 7,470,236 B1 | 12/2008 | Kelleher et al. | |
| 2002/0007198 A1 | 1/2002 | Haupert et al. | |
| 2002/0183805 A1 | 12/2002 | Fang et al. | |
| 2003/0088289 A1 | 5/2003 | Levine et al. | |
| 2003/0120324 A1 | 6/2003 | Osborn et al. | |
| 2003/0208246 A1 | 11/2003 | Kotlik et al. | |
| 2004/0059395 A1 | 3/2004 | North et al. | |
| 2004/0098063 A1 | 5/2004 | Goetz | |
| 2004/0116978 A1 | 6/2004 | Bradley | |
| 2004/0158119 A1 | 8/2004 | Osorio et al. | |
| 2005/0033386 A1 | 2/2005 | Osborn et al. | |
| 2005/0113887 A1 | 5/2005 | Bauhahn et al. | |
| 2005/0245991 A1 | 11/2005 | Faltys et al. | |
| 2006/0161214 A1 | 7/2006 | Patel | |
| 2006/0241721 A1 * | 10/2006 | Kothandaraman et al. | 607/46 |

FOREIGN PATENT DOCUMENTS

| | | |
|---|---|---|
| WO | WO 2004/004412 | 1/2004 |
| WO | WO 2004/036377 | 4/2004 |

OTHER PUBLICATIONS

Office Action dated Jan. 24, 2008 for U.S. Appl. No. 11/222,495 (12 pgs.).

Notification of Transmittal of the International Search Report and the Written Opinion, dated Feb. 9, 2007 for corresponding PCT Application No. PCT/US2006/034880, filed on Sep. 7, 2006, 13 pgs.

Office Action dated Jul. 12, 2007 for U.S. Appl. No. 11/222,495 (11 pgs.).

Notification of Transmittal of the International Preliminary Report on Patentability, dated Aug. 6, 2007 for corresponding PCT Application No. PCT/US2006/034880 (11 pgs.).

Response to Office Action dated Aug. 28, 2008 for U.S. Appl. No. 11/222,495 (30 pgs.).

Office Action dated May 28, 2008 for U.S. Appl. No. 11/222,495 (12 pgs.).

Office Action dated Nov. 26, 2008 for U.S. Appl. No. 11/222,495 (12 pgs.).

Responsive Amendment dated Feb. 24, 2009 for U.S. Appl. No. 11/222,495 (28 pgs.).

Notice of Allowance date Feb. 12, 2009 for U.S. Appl. No. 11/222,495 (5 pgs.).

* cited by examiner

EXTERNAL PRESENTATION OF ELECTRICAL STIMULATION PARAMETERS

TECHNICAL FIELD

The invention relates to medical devices and, more particularly, medical devices for delivery of electrical stimulation therapy via implanted electrodes

BACKGROUND

Electrical stimulation devices are used to deliver neurostimulation therapy to patients to treat a variety of symptoms or conditions such as chronic pain, tremor, Parkinson's disease, epilepsy, incontinence, sexual dysfunction, obesity, or gastroparesis. Neurostimulation may involve delivery of electrical pulses via one or more implantable leads that include electrodes located proximate to the spinal cord, pelvic nerves, or stomach, or within the brain of a patient. The electrical stimulation device includes a pulse generator, which may be implantable or external.

A clinician programs the electrical stimulation device to define one or more stimulation programs. Each program may specify stimulation pulse parameters such as voltage or current amplitude, pulse width and pulse rate, as well as electrode combinations and polarities. Some stimulation devices may deliver stimulation pulses via two or more leads, each of which may carry numerous electrodes. The clinician selects combinations of electrodes, on a single lead or among multiple leads, for delivery of stimulation pulses. In this manner, the clinician can direct stimulation energy to a particular stimulation site.

SUMMARY

In general, the invention is directed to external indication of electrical stimulation parameters. An external indicator device presents parameters associated with stimulation therapy generated by a pulse generator, which may be associated with an external or implantable stimulation device. In this manner, the external indicator device enables a user to visualize stimulation parameters without actually delivering stimulation therapy to a patient via implanted electrodes. The electrical stimulation parameters may include electrical amplitude levels, pulse widths, pulse rates, electrode combinations, and electrode polarities for stimulation generated by the pulse generator.

The external indicator device presents the electrical parameters via an array of indicators. The indicators may be activated with an intensity or other visual characteristics in proportion to the parameter level. The indicators may be physically arranged to represent the relative positions of electrodes carried by one or more implantable leads. The indicators may be indicator lights, such as light emitting diodes (LEDs). As an alternative, the indicators may be graphically presented by a pixelized display device, such as a liquid crystal display (LCD) or plasma display.

By electrically coupling the output terminals of the pulse generator to the external indicator device, a user is able to visualize delivery of stimulation pulses across electrodes carried by a lead. The ability to visualize delivery of stimulation pulses using an external indicator device may be especially useful in an educational or training setting. Also, the external indicator device may be used by technical personnel in the field for demonstration or trouble-shooting purposes. In each case, the external indicator device may be made small and compact for convenient portability.

In one embodiment, the invention provides a method comprising receiving electrical stimulation pulses applied by a pulse generator across a set of output terminals, and indicating one or more parameters associated with the electrical stimulation pulses via an array of visual indicators, wherein each of the indicators corresponds to one of the output terminals.

In another embodiment, the invention provides a device comprising an array of visual indicators that indicate one or more parameters associated with electrical stimulation pulses generated by a pulse generator across a set of output terminals, and an interface that electrically couples the indicators to output terminals associated with the pulse generator, wherein each of the indicators corresponds to one of the output terminals.

In an additional embodiment, the invention provides a system comprising a pulse generator that generates electrical stimulation pulses across a set of output terminals, an indicator device having an array of visual indicators that indicate one or more parameters associated with the electrical stimulation pulses generated by a pulse generator, and an interface that electrically couples the indicators to the output terminals, wherein each of the indicators corresponds to one of the output terminals.

The indicators may be physically arranged to represent relative positions of electrodes carried by one or more implantable leads. In some embodiments, for example, the indicators may be arranged as a first column of indicators representing electrodes carried by a first implantable lead, and a second column of indicators representing electrodes carried by a second implantable lead.

The parameters may include at least one of electrical voltage, electrical current, electrical energy, pulse width, pulse rate, and polarity. The indicators may include indicator lights, the method further comprising activating the indicator lights as a function of the stimulation pulses applied across the corresponding terminals. For example, the corresponding indicator lights may be activated with an intensity proportional to one or more of the parameters.

In some embodiments, each of the indicators includes a first indicator light and a second indicator light, the first indicator light being activated to indicate positive polarity and activating the second indicator light being activated to indicate negative polarity. For example, the first indicator light may include a first light emitting diode and the second indicator light may include a second light emitting diode. In this case, the first and second light emitting diodes are coupled in parallel with opposite polarities such that the first light emitting diode activates in response to a positive voltage and the second light emitting diode activates in response to a negative voltage. In other embodiments, the indicators may be graphically presented by a pixelized display device.

To facilitate visualization of the pulse parameters, the electrical stimulation pulses may be generated at a substantially slower pulse rate and a substantially longer pulse width than electrical stimulation pulses typically selected to provide stimulation therapy to a patient, thereby facilitating visual indication of the electrical parameters.

The invention may provide a number of advantages. For example, the external indicator device permits a user to readily and intuitively visualize the delivery of stimulation therapy. The external indicator device may be conveniently coupled to the output terminals of a pulse generator, either directly or via one or more adapters. In addition, the external indicator device may be sized as a small, portable device to permit ready transportation. In some embodiments, the external indicator device may be handheld. Consequently, the external indicator device may be particularly useful in an educational, training, marketing, sales or support environment to facilitate visualization of stimulation parameters without actually delivering stimulation therapy to a patient via implanted electrodes.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
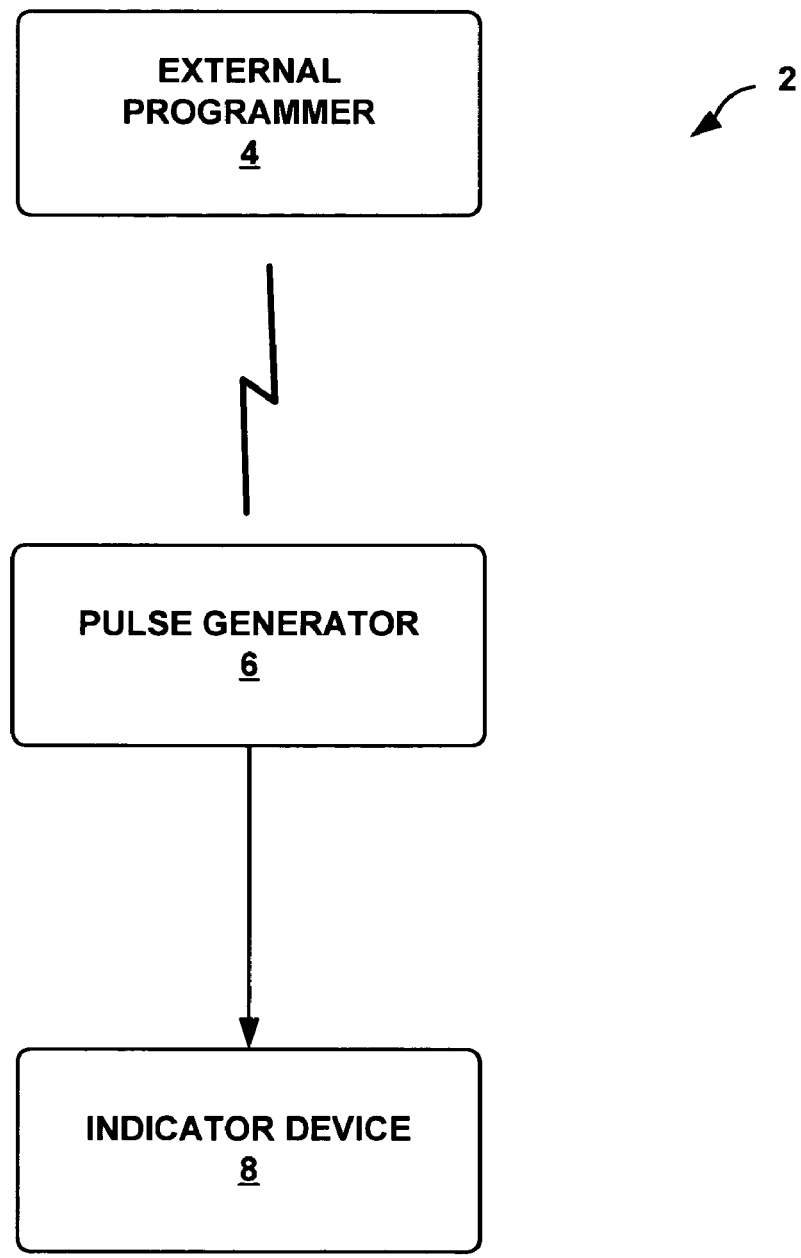
FIG. 1 is a block diagram illustrating an example system for indicating electrical stimulation pulse parameters in accordance with the invention.

FIG. 1 is a diagram illustrating a system 2 for indicating electrical parameters associated with stimulation therapy pulses generated by pulse generator 6. In general, system 2 may be used in an educational, training, marketing or sales environment to visualize delivery of stimulation therapy to a patient. System 2 visually indicates stimulation parameters, such as a current- or voltage-controlled amplitude, pulse rate, pulse width, electrode combinations, and polarities for stimulation therapy generated by system 2. In this manner, system 2 provides an intuitive indication of stimulation parameters, thereby enabling a clinician to visualize stimulation parameter without actually delivering stimulation therapy to a patient via implanted electrodes.

As shown in FIG. 1, system 2 includes an external programmer 4, a pulse generator 6, and an external indicator device 8. Pulse generator 6 generates electrical stimulation in the form of electrical pulses according to one or more stimulation programs that define applicable stimulation parameters. A clinician, physician, or other authorized user may program pulse generator 6 to generate stimulation therapy via external programmer 4. Specifically, a clinician or physician may operate external programmer 4 to select particular programs or parameter values applied by pulse generator 6.

External programmer 4 communicates with pulse generator 6 by a wireless or wired connection and may have a simple user interface, such as a button or keypad, and a display or lights. External programmer 4 may comprise a clinician programmer or other programming device. In any case, external programmer 4 may generally be a hand-held device configured to permit activation of stimulation and adjustment of stimulation parameters as well as being capable of turning stimulation on or off. In some embodiments, pulse generator 6 may include a series of buttons, switches, or a small display.

In this case, external programmer 4 may not be needed to program pulse generator 6 or external programmer 4 may be used in addition to the controls located on pulse generator 6.

Pulse generator 6 may comprise a trial stimulator or other external stimulator and generates electrical stimulation in accordance with one or more programs selected by the clinician via external programmer 4. Alternatively, pulse generator 6 may be an implantable stimulator that is used externally for demonstration or training purposes. Pulse generator 6 generates electrical pulses with the voltage or current amplitude, pulse rate, pulse width, and polarity on an array of channels.

When one or more leads (not shown) are coupled to pulse generator 6, the electrical pulses may be delivered to a patient generator 6 (not shown) via the implanted electrodes. However, when indicator device 8 is electrically connected to pulse generator 6, the stimulation therapy generated by pulse generator 6 causes indicator device to present an indication of one or more applicable stimulation parameters. In this manner, indicator device 8 permits a user to visualize the simulated delivery of electrical stimulation pulses among an array of implanted electrodes.

Indicator 8 includes an array of indicators, such as indicator lights. The indicator lights are activated to produce an intensity, or other visual characteristic, in proportion to the stimulation therapy. Alternatively, in other embodiments, indicator device 8 may include a pixelized display that graphically presents an array of indictors. In either case, the indicators may be physically arranged to represent relative positions of electrodes carried by one or more implantable leads. In some embodiments, for example, the indicators may be arranged as a first column of indicators representing electrodes carried by a first implantable lead, and a second column of indicators representing electrodes carried by a second implantable lead.

Indicator device 8 may comprise an array of light emitting diodes (LEDs) that produce an intensity or brightness in proportion to voltage or current amplitude, pulse rate, or pulse width of the stimulation parameters. As an alternative, the LEDs may emit pulses of light or "blink" at a frequency in proportion to the voltage or current amplitude, pulse rate or pulse width of the stimulation pulses. For example, the LEDs may be brighter or blink more frequently as amplitude, pulse rate or pulse width increases.

Each indicator may correspond to one of the output terminals of the pulse generator 6. Each output terminal corresponds to one of the electrodes that would be carried by a lead. The electrodes would be electrically coupled to the output terminals via conductors carried by a lead. In addition to indicating parameters such as amplitude, pulse rate, or pulse width, indicator device 8 may be configured to indicate the polarity of the stimulation pulses applied at the respective output terminals. As an example, each indicator may include a pair of LEDs connected in parallel with one another, but with opposite polarities. One LED in the pair activates in response to a positive voltage, while the other LED activates in response to a negative voltage. In this manner, an output terminal can be identified as either a cathode or anode. The LEDs in each pair may have different colors, such as red and green, to indicate different polarities, e.g., cathode or anode.

Each indicator light within indicator device 8 corresponds to one output terminal of pulse generator 6 and may comprise a pair of LEDs. As discussed above, each pair of LEDs may be connected in parallel with opposite polarity. Thus, one LED of the pair of LEDs activates in proportion to the electrical stimulation when the corresponding output terminal of pulse generator 6 acts as an anode and the other LED of the pair of LEDs activates in proportion to the electrical stimulation when the corresponding output terminal of pulse generator 6 acts as a cathode. Specifically, the appropriate LED in the pair of LEDs emits light with intensity in proportion to the voltage or current amplitude of electrical stimulation and emits the light on a periodic basis for a duration of time in proportion to the pulse rate and pulse width of the electrical stimulation, respectively.

Additional circuitry or circuit components may be electrically connected to indicator device 8 to improve performance. For example, each of the LED pairs within indicator device 8 may be electrically connected in parallel with a resistive element, such as a resistor, to provide a leakage path for out of regulation current, such as transients or other noise. Additionally, a resistor may be electrically connected in series between each LED pair and the corresponding terminal of pulse generator 6 to establish a turn-on threshold. Electrical stimulation that exceeds the turn-on threshold, i.e., the diode bias voltage, activates the corresponding indicator light within array 8. The resistor may be selected to set a turn-on threshold value that prevents leakage current or a "return current" after a stimulation pulse from activating one of the indicator lights. Return currents are typically generated after capacitively coupled stimulation pulses are delivered to equalize the circuit. By eliminating erroneous activation due to leakage current, return current after a stimulation pulse, or other effects from pulse generator 6, an accurate representation of the electrical stimulation generated by pulse generator 6 is ensured.

In order to ensure an accurate representation of the electrical stimulation generated by pulse generator 6, the series resistor may be selected to have a resistive value approximately equal to the expected impedance at the electrode that is connected to the corresponding terminal for delivering stimulation therapy to a patient. In other words, the resistor is selected to have a resistive value matching the impedance of a nominal patient so that pulse generator 6 delivers stimulation therapy in substantially the same fashion as when delivering stimulation therapy to a patient via electrodes. As an example, pulse generator 6 may be prevented from delivering therapy with out of regulation current because the headroom is limited by the resistor.

In any case, because electrical pulses are normally delivered at a rate faster than can be perceived or detected by the human eye, a clinician may program pulse generator 6, via external programmer 4, to generate electrical stimulation at a substantially slower rate than is ordinarily chosen for treating symptoms of a patient. For example, a clinician may program pulse generator 6 to generate electrical pulses at a rate of approximately 1-2 Hz. For purposes of comparison, a pulse generator 6 may deliver electrical pulses at a rate of 1 to 100 Hz, depending on the particular therapy application. In addition, pulse generator 6 may be programmed to generate electrical pulses with a substantially longer pulse width, than the pulse width ordinarily used for therapy, so that the electrical pulses are long enough to be detected by the human eye. In general, pulse generator 6 may be programmed to generate electrical pulses at a pulse rate and with a pulse width that can easily be perceived by the human eye. Other stimulation parameters such as amplitude, electrode combinations, or polarity may not need to be changed from standard values.

In general, indicator device 8 indicates the electrical current, pulse rate, and pulse width as well as the direction of current generated at each output terminal of pulse generator 6. The number of indicators lights within the array of indicators is typically equal to the number of output terminals provided by pulse generator 6, although a lesser number of indicators may be used if the pulse generator is programmed to use only a subset of the output terminals. In general, there is a one-to-one correspondence between indicators and output terminals. As mentioned above, however, each indicator may include a pair of LEDs, such that there are two LEDs of opposite polarities for every output terminal.

Indicator device 8 may be contained within a housing sized to conform to a portable, handheld device. The housing may be formed with a coupling interface in the form of an electrical connector, such as a plug or socket, for receiving a cable or wire to couple the array of indicator lights to the output terminals of pulse generator 6. Alternatively, as will be described, indicator 8 may be coupled to an array of electrodes on one or more leads coupled to the output terminals of pulse generator 6. In this case, each of the indicator lights may be electrically connected to a corresponding electrode on the distal end of the lead. In this case the lead is connected to the pulse generator and may be capable of delivering electrical stimulation. Rather than implanting the lead, however, the lead is used externally to couple electrical stimulation from pulse generator 6 to indicator device 8. The housing may be constructed of materials such as polyurethane, polycarbonate, aluminum, and other durable plastic, polymeric, or metal alloy materials sufficient to secure and protect the inner components of indicator device 8.

System 2 may be used in a training, marketing or sales environment to demonstrate the programming or electrical stimulation capabilities of pulse generator 6 and external programmer 4. Alternatively, system 2 may be used for technical support to verify proper operation of pulse generator 6. In either case, pulse generator 6 may be programmed to deliver stimulation therapy according to a plurality of time-interleaved or simultaneous stimulation programs. In another example, pulse generator 6 may be programmed to ramp stimulation therapy up or down or shift stimulation between different combinations of electrodes. In any case, system 2 simultaneously indicates the stimulation parameters for stimulation therapy generated on each output terminal of pulse generator 6. Specifically, system 2 may be particularly advantageous for indicating electrode combinations and polarities of the selected electrodes for stimulation therapy defined by one or more programs. Consequently, system 2 may enable a clinician to better understand and visualize the programming and electrical stimulation capabilities of pulse generator 6.

Figure 2:
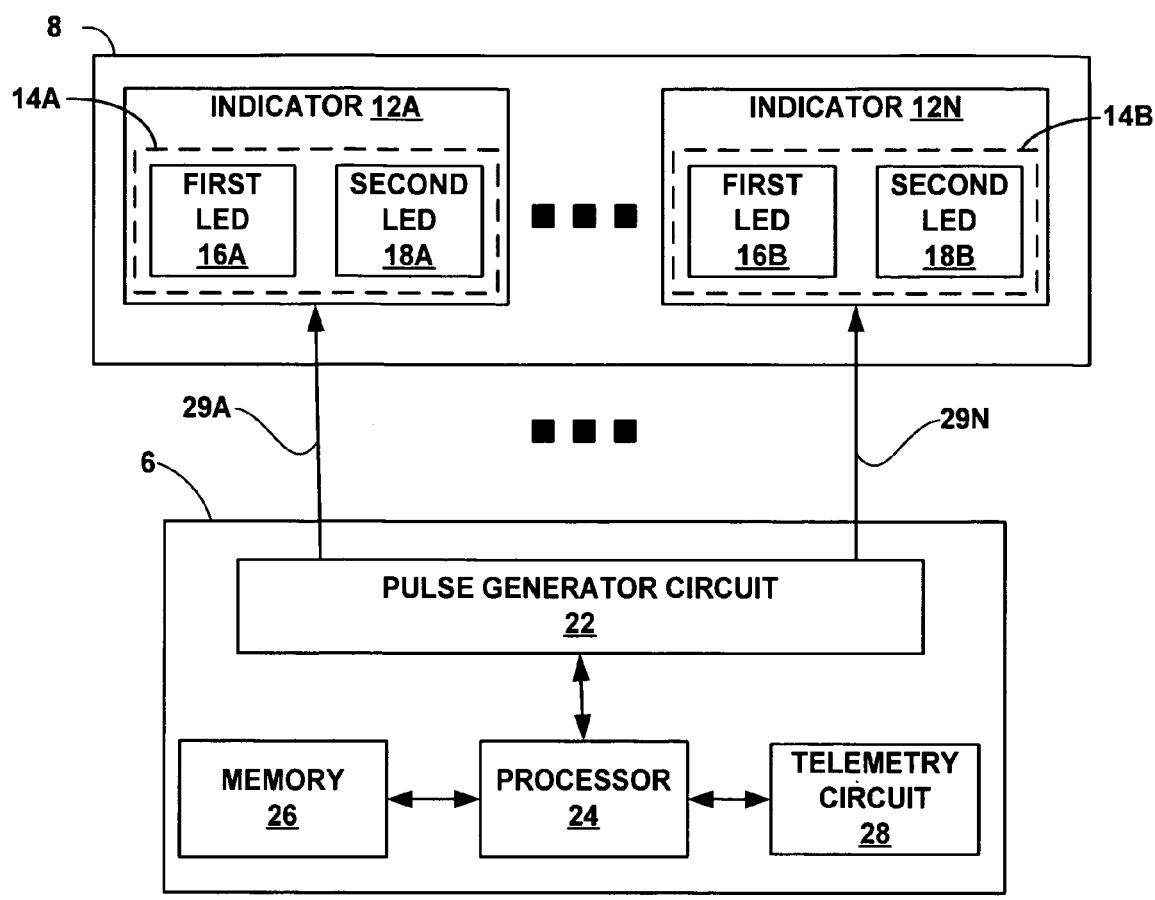
FIG. 2 is a block diagram illustrating an example indicator device coupled to a pulse generator in accordance with an embodiment of the invention.

FIG. 2 is a block diagram illustrating an example configuration of an indicator device 8 coupled to a pulse generator 6. Pulse generator 6 generates stimulation therapy in the form of electrical pulses and indicator device 8 indicates stimulation parameters for the electrical stimulation in proportion to the stimulation therapy. Indicator device 8 may be directly coupled to pulse generator 6 to assist or aid a clinician or physician to visualize the delivery of electrical stimulation in a training, marketing, sales or support environment. As shown in FIG. 2, pulse generator 6 includes a pulse generator circuit 22, a processor 24, memory 26, and a telemetry circuit 28. Pulse generator circuit 22 may be coupled to a power source such as a battery (not shown) and may generate electrical pulses on at least some of the output terminals of under the control of processor 24.

Processor 24 controls pulse generator circuit 22 to deliver stimulation therapy according to one or more programs. Specifically, processor 24 may control pulse generator circuit 22 to deliver electrical pulses with a voltage or current amplitude, a pulse rate, and a pulse width. Processor 24 may also control pulse generator circuit 22 to deliver the pulses via a selected subset of output terminals with selected polarities, as specified by the selected programs. Processor 24 may control pulse generator circuit 22 to deliver each pulse according to a different program. Processor 24 may include a microprocessor, a controller, a digital signal processor (DSP), an application specific integrated circuit (ASIC), a field programmable gate array (FPGA), discrete logic circuitry, or the like.

Memory 26 may store programs that are available to be selected by a clinician for delivery of electrical stimulation therapy, e.g., via an external programmer 4 (FIG. 1). In some embodiments, memory 26 may also store or record usage information in memory 26. Memory 26 may include any volatile, non-volatile, fixed, removable, magnetic, optical, or electrical media, such as a random access memory (RAM), read-only memory (ROM), compact disc (CD-ROM), hard disk, removable magnetic disk, memory cards, electrically erasable (EEPROM), flash memory, and the like.

Telemetry circuit 28 allows processor 24 to communicate with an external programmer 4, such as a clinician programmer or other device suitable for pulse generator 20. Processor 24 may receive programs to test on a patient from the external programmer via telemetry circuit 28 during programming by a clinician, a physician, or other authorized user. The programs received during programming by a clinician may be stored in memory 26.

Indicator device 8 is electrically coupled to the output terminals of pulse generator 6 and includes indicator lights 12A-N (collectively indicator lights 12) to indicate stimulation parameters of stimulation therapy generated by pulse generator 6. In particular, each of indicator lights 12 corresponds to an output terminal 29A-29N (collectively output terminals 29) of pulse generator 20. Consequently, each indicator light 12 represents an electrode on a lead that may be coupled to output terminals 29 of pulse generator 6 to deliver stimulation to a patient. Typically, the number of indicator 12 within indicator device 8 corresponds to the number of output terminals 29 of pulse generator 6.

Each of indicators 12 may comprise a pair of LEDs 14A-N (collectively "LED pairs 14") that includes a first LED 16A-N (collectively "first LEDs 16") and a second LED 18A-N (collectively "second LEDs 18"). First and second LEDs 16 and 18 are coupled in parallel to each other with opposite polarity. LEDs 16 activate in proportion to electrical stimulation generated on a corresponding output terminal 29 of pulse generator 20 when the output terminal acts as an anode. LEDs 18 activate in proportion to electrical stimulation generated when the corresponding output terminal 29 acts as a cathode. In some embodiments, LEDs 28 may comprise an LED that emits green light in proportion to the electrical stimulation and LEDs 16 may comprise an LED that emits red light in proportion to the electrical stimulation.

When pulse generator 6 generates stimulation therapy on one or more channels, the appropriate one of LEDs 16 and 18 emit pulses of light or "blink" in proportion to the electrical current or voltage amplitude, pulse rate, and pulse width in proportion to the stimulation therapy. For example, the appropriate one of LEDs 16 and 18 emits light with intensity in proportion to the voltage or current amplitude of electrical stimulation on the corresponding channel of pulse generator 6 and emits the in pulses on a periodic basis for a duration of time proportional to the pulse rate and pulse width of the stimulation therapy.

Because pulse generator 6 may generate electrical pulses at a rate faster than can be perceived or detected by the human eye to treat symptoms of a patient, a clinician, physician, or other authorized user may program pulse generator 260, via an external programmer, to generate electrical stimulation at a substantially slower rate than is effective for treating symptoms of a patient. For example, as mentioned previously, a clinician may program pulse generator 20 to generate electrical pulses at a rate of approximately 1-2 Hz. In particular, pulse generator 6, indicator device 8, or both, may include a pulse rate selector or clock divide device with which a clinician can interact to select the pulse rate. More specifically, the clock divide device may comprise a turn knob or set of buttons that scale the pulse rate based on input received from a clinician. For example, as a clinician rotates the turn knob in one direction, the pulse rate may reduce in proportion to the number of rotations and as the clinician rotates the turn knob in the opposite direction, the pulse rate increases in proportion to the number of rotations. The set of buttons may comprise a first and a second button that increase and decrease the pulse rate in proportion to the number of times the button is depressed, respectively. Each time one of the buttons is depressed, the pulse rate may be increased or decreased logarithmically, by a factor of ten, or in proportion to other scales. In addition, the turn knob and set of buttons may be configured so that the pulse rate may not exceed a maximum pulse rate, such as the initially programmed pulse rate, or drop below a minimum pulse rate, such as 1 Hz. Pulse generator 6 may also be programmed to generate electrical pulses with a substantially longer pulse width so that the electrical pulses are long enough to be detected by the human eye. Accordingly, pulse generator 6, indicator device 8, or both may also include a device similar to the pulse rate selector with which a clinician may interact to select the pulse width of the stimulation therapy generated by pulse generator 6. In some embodiments, processor 24 may control pulse generator circuit 22 to deliver stimulation therapy at a pulse rate and a pulse width that can be easily perceived by the human eye.

As an example, a "display" or "demonstration" program may be stored in memory 26 of pulse generator 6. The display program may globally set or define a range of pulse rates and pulse widths suitable for indicating stimulation parameters in a training, marketing, sales or support environment. In particular, a clinician, physician, or other authorized user may program or select pulse rates and pulse widths from a range of standard values, but the display program may process the selected values to generate stimulation therapy at a pulse rate and pulse width as a function of the selected values, but at pulse rate and width that can be perceived by the human eye. The display program adjusts the programmed pulse rates and pulse widths to be slower and longer, respectively, so that the delivery of stimulation pulses can be better visualized by the user. Thus, pulse generator 6 may effectively operate in a "display" mode that enables a clinician to better understand and visualize the programming and stimulation therapy capabilities of pulse generator 20.

Indicator device 6 may also include additional circuitry or circuit components to improve the performance of array 10. For example, a resistor may be electrically connected in parallel with each of first and second LEDs 16 and 18 that form indicator lights 14 to provide a leakage path for out of regulation current, such as transients or other noise. Additionally, a resistor may also be electrically connected in series with each of indicator lights 14 and the corresponding channel of pulse generator 20 to establish a turn on threshold for activating LEDs 16 Thus, leakage currents, return currents, and other effects from pulse generator 6 are less likely to activate indicator lights 14 and misrepresent the stimulation therapy generated by pulse generator 6

Figure 3:
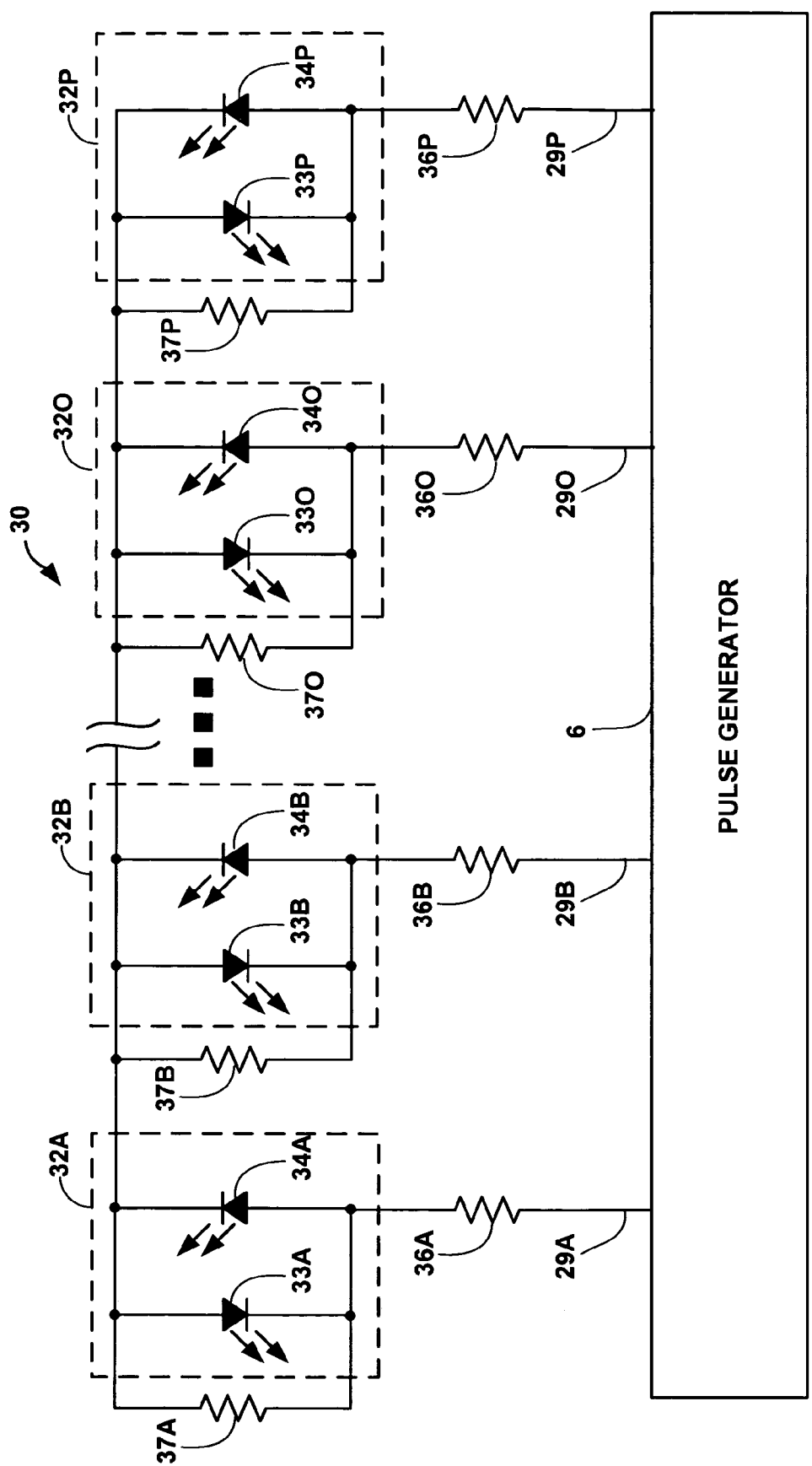
FIG. 3 is a schematic diagram illustrating a circuit that indicates electrical parameters for stimulation therapy via an array of indicator lights.

FIG. 3 is a schematic diagram illustrating a circuit 30 suitable for use as an array of indicator lights that indicate stimulation parameters for stimulation therapy generated by pulse generator 6. Circuit 30 may be electrically connected to pulse generator 6 via a wire or cable and indicates stimulation parameters for the stimulation therapy generated by pulse generator 38. In the example of FIG. 3, circuit 30 is configured for sixteen output terminals, i.e., sixteen electrodes. Accordingly, circuit 30 includes indicators 32A-P (collectively indicators 32), of which indicators 32A, 32B, 32O and 32P are shown. Each indicator 32 emits lights or "blinks" in proportion to the stimulation therapy generated on the corresponding output terminals 29A-29P of pulse generator 38.

Each of indicators 32 comprises a pair of LEDs that includes a first and a second LED, i.e., LEDs 33A-P and LEDs 34A-P, electrically connected in parallel to each other with opposite polarity. Thus, when pulse generator 6 generates stimulation therapy, one of LEDs 33A-P and LEDs 34A-P in a corresponding pair of LEDs is activated in proportion to the stimulation therapy generated by pulse generator 6. As an example, LEDs 33A-P may comprise LEDs that emit green light when activated to indicate that the corresponding output terminal 29 of pulse generator 6 acts as a cathode and LEDs 34A-N may comprise LEDs that emit red light when activated to indicate that the corresponding output terminal 29 of pulse generator 38 acts as an anode.

Because indicators 32 are directly connected to output terminals 29 of pulse generator 6, indicators 32 are driven by the output terminals and are activated in proportion to the stimulation therapy generated by pulse generator 6. In some embodiments, however, output terminals 29 may be directly connected to optoisolators (not shown) which drive indicators 32. Because indicators 32 are formed from pairs of LEDs 33A-P and LEDs 34A-P in FIG. 3, the appropriate one of LEDs 33A-N and LEDs 34A-N in each of indicators 32 emits light in pulses proportional to the electrical pulses that form the stimulation therapy. In other words, indicators 32 "blink" at a rate and with a duration in proportion to the pulse rate and pulse width of stimulation therapy generated by pulse generator 38 and with intensity proportional to the voltage or current amplitude and emits the light in pulses.

Resistors 36A-P may also be connected in parallel with LEDs 33A-P and 34A-P, respectively. Resistors 36A-P serve to provide a leakage path for out of regulation current, such as transients or other noise. Thus, resistors 36A-P may prevent out of regulation current generated by pulse generator 38 from damaging indicators 32. Circuit 30, and more particularly, indicators 32, may be electrically connected to electrodes on one or more leads coupled to pulse generator 38 in some embodiments. In such embodiments, resistors 36A-P may serve to prevent out of regulation currents from damaging electrodes on the leads.

Resistors 37A-P (collectively resistors 37) may also be connected in series with indicators 32, respectively. Resistors 37 may be selected to set a turn-on threshold to prevent leakage current or return current after a stimulation pulse from activating LEDs 33A-P and LEDs 34A-P. Resistors 37 may be selected so that standard stimulation therapy amplitudes exceed the turn-on threshold and, thus, activate LEDs 33A-P and LEDs 34A-P and nominal leakage currents, return currents, or other effects generated by pulse generator 38 do not exceed the turn-on threshold and, thus, do not activate LEDs 33A-P and LEDs 34A-P.

Resistors 37 may be selected to have a resistive value approximately equal to the expected impedance at the electrode that is connected to the corresponding terminal for delivering stimulation therapy to a patient. In other words, each of resistors 37 is selected to have a resistive value matching the impedance of a nominal patient so that pulse generator 38 delivers stimulation therapy in substantially the same fashion as when delivering stimulation therapy to a patient via electrodes. Consequently, pulse generator 38 may be prevented from delivering therapy with out of regulation current because the headroom is limited by resistors 37.

As shown in FIG. 3, each indicator 32 is connected in parallel with adjacent indicators 32. If output terminal 29A serves as a cathode and output terminal 29P serves as an anode, then current flows from output terminal 29A to indicator 32A, then from indicator 32A to indicator 32P, and then from indicator 32P to output terminal 29P. In this case, output terminal 29A forms a high voltage potential or current source, while output terminal 29P forms a low voltage potential or current sink. Other output terminals form open circuits. Consequently, other indicators 32 are not activated.

In many cases, however, more than two output terminals may be simultaneously activated by pulse generator 6. For example, a group of output terminals may be combined to share anodic or cathodic duties. In addition, different parallel electrode combinations may be used to deliver different stimulation programs, either on a simultaneous or interleaved, time-multiplexed basis. In each case, stimulation energy delivered by pulse generator 6 is applied via selected output terminals 29 to one of more indicators 32 and returns to other output terminals via one or more other indicators.

Generally, circuit 30 is used in a training, marketing, sales or support environment to assist a clinician or physician in visualizing stimulation parameters for stimulation therapy generated by pulse generator 6. Therefore, indicators 32 may be positioned or arranged within a housing to reflect or correspond to an arrangement of electrodes on one or more leads to further assist the clinician in visualizing the delivery of stimulation therapy. For example, indicators 32 may include four or eight pairs of LEDs 37 arranged in a single column or row to provide a clinician with a visual representation of electrodes on a single lead. In another example, to provide a clinician with a visual representation of electrodes on a pair of leads, indicators 32 may include eight or sixteen pairs of LEDs 37 arranged in two columns or rows. In either case, the indicators may be physically arranged to represent relative positions of electrodes carried by one or more implantable leads. Consequently, circuit 30 and, more particularly, indicators 32, may provide a more intuitive representation for delivery of stimulation therapy.

Figure 4A:
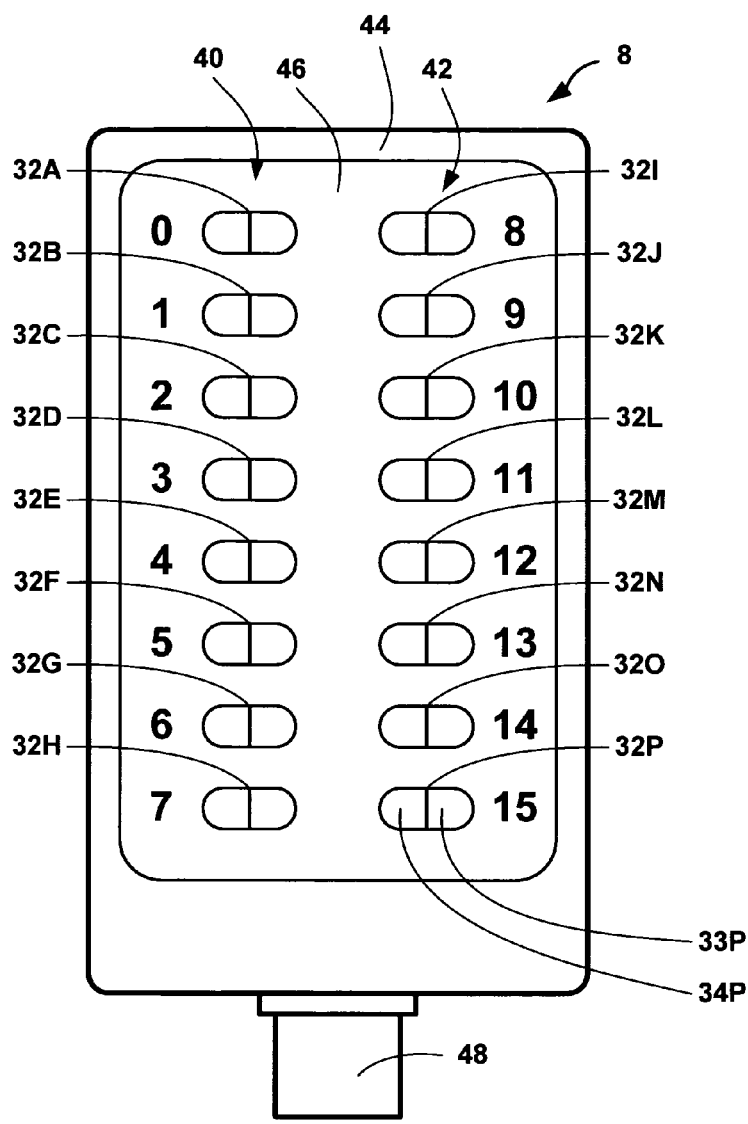
FIGS. 4A and 4B are diagrams illustrating an exemplary embodiment of an indicator device in accordance with an embodiment of the invention.
Figure 4B:
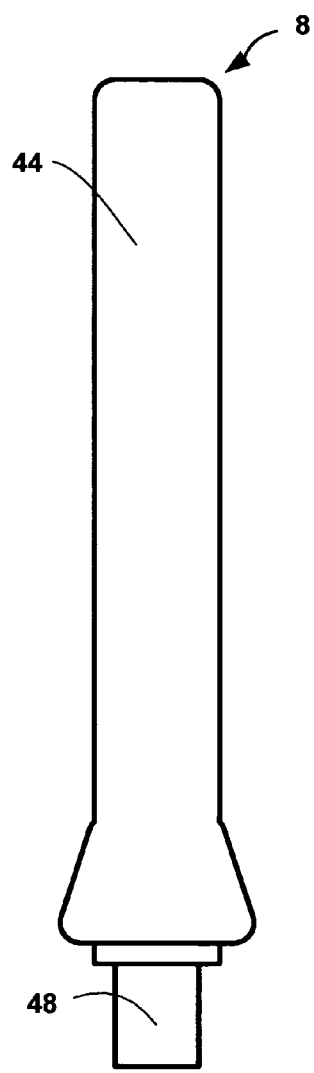

FIGS. 4A and 4B are front and side views, respectively, of an exemplary indicator device 8 that indicates stimulation parameters for stimulation therapy according to an embodiment of the invention. In general, indicator device 8 may be coupled to a pulse generator (not shown) and used in a training, marketing, sales or support environment. Electrical connector 48 receives a wire or cable that couples indicator device 8 to output terminals associated with a pulse generator. More specifically, each output terminal of the pulse generator is actively coupled to a corresponding indicator 32A-32P that indicates electrical parameters, i.e., voltage or current amplitude levels, pulse widths, pulse rates, electrode combinations, and polarities of electrodes, for stimulation therapy generated on the channel.

As shown in FIG. 4A, indicator device 8 includes an array of indicators 32 arranged in two columns 40, 42. Each column 40, 42 includes eight indicators 32 in the example of FIG. 4A. Each indicator 32 includes a pair of LEDs 33, 34 electrically connected in parallel with opposite polarity. For example, indicator 32P includes LEDs 33P, 34P. One LED 33 in each indicator 32 may emit green light when activated, while the other LED 34 that emits red light when activated. Accordingly, when the corresponding output terminals of the pulse generator act as cathodes, the corresponding green LEDs of indicator indicators 32 activate in proportion to the stimulation therapy. When the channels of the pulse generator act as anodes, the corresponding red LEDs of indicators 32 activate in proportion to the stimulation therapy.

In the example of FIG. 4A, indicators 32A-H in first column 40 represent a set of eight electrodes on a first lead and indicator 32I-P in second column 42 represent a set of electrodes on a second lead. Indicators 32A-H are designated electrodes 0-7 and indicators 32I-P are designated 8-15. Consequently, indicator device 8 can provide a visual representation of stimulation therapy delivered to a patient via two eight-electrode leads. As a result, indicator device 40 may provide a clinician or physician an intuitive visual representation of stimulation therapy, including the direction, shape or strength of a stimulation field that would be established by multiple electrodes.

As shown in FIGS. 4A and 4B, housing 44 of indicator device 8 may be handheld and portable. Housing 44 can be constructed from materials such as such as polyurethane, polycarbonate, aluminum, and other durable plastic, polymeric, or metal alloy materials sufficient to secure and protect indicators 32 and other circuit components. The front face 46 of indicator device 8 may be sufficiently transparent so that a user can see the light emitted by indicators 32 during operation. Alternatively, front face 46 may include an array of apertures through which indicators 32 are visible.

Figure 5:
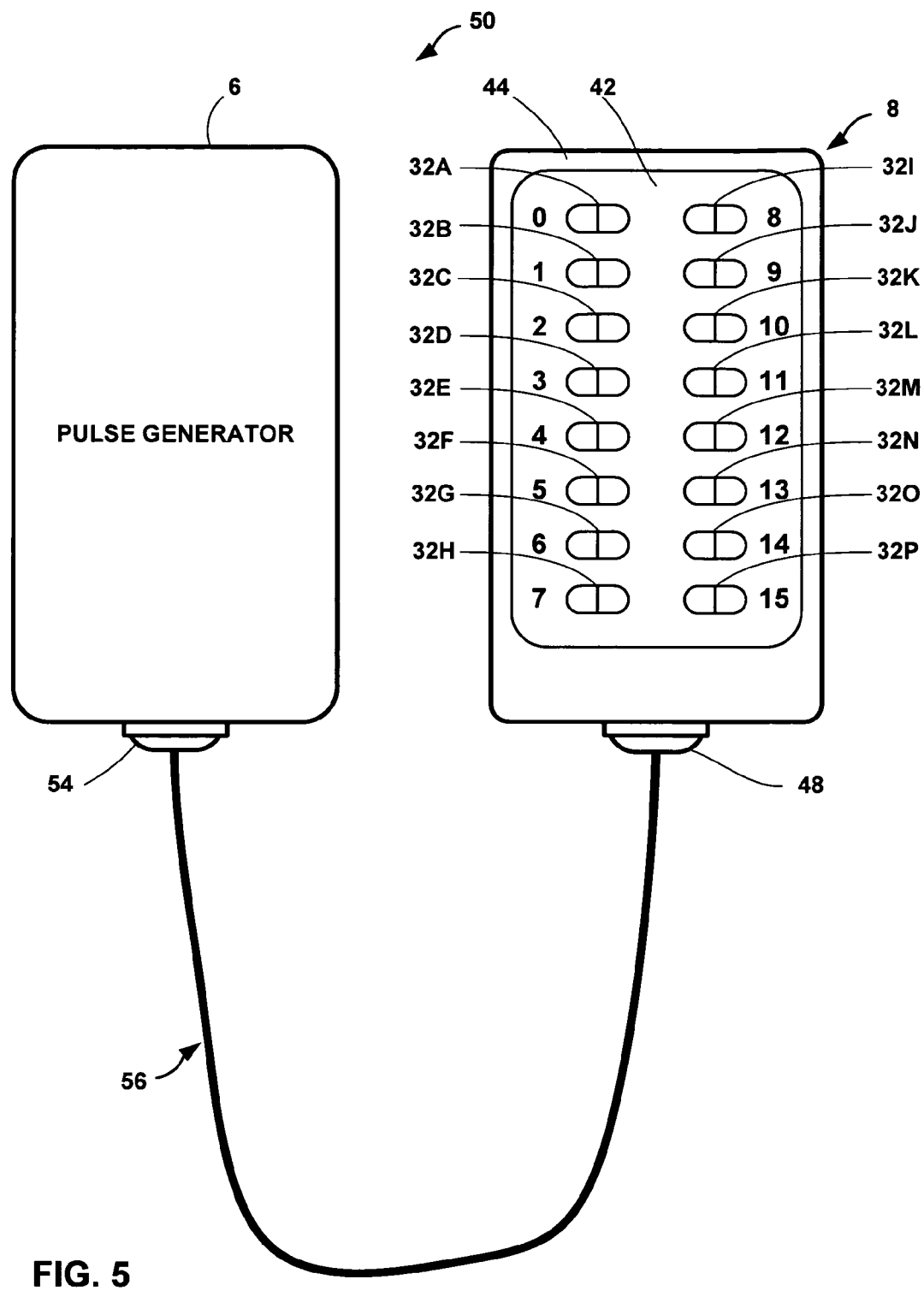
FIG. 5 is a diagram illustrating a pulse generator coupled to an external indicator device.

FIG. 5 is a diagram illustrating a system 50 that provides a visual representation of stimulation parameters for stimulation therapy generated by pulse generator 52. System 50 incorporates pulse generator 6 and indicator device 8, electrically coupled to one another via an electrical coupling interface. For example, indicator device 8 is coupled to pulse generator 6 via a wire or cable 56 that is received by electrical connectors 54 and 38 of pulse generator 6 and indicator device 8, respectively. The electrical coupling interface may be constructed in any manner sufficient to couple respective output terminals to drive corresponding indicators. In some embodiments, electrical connectors 54 and 38 may be male or female and may take the form of an integrated connector or a set of contacts or terminals.

Pulse generator 6 may be equipped with an integrated electrical connector the presents the output terminals as an array of connector contacts, particularly if the pulse generator is an external stimulator, e.g., for trial screening. If pulse generator 6 does not include an integrated connector, but instead provides a connector block for connection to one or more implantable leads, an adapter can be provided. For example, a proximal end of the lead may be coupled to the connector block of pulse generator 6, while a distal end of the lead may be coupled either directly to indicator device 8 or to an adapter cable that couples to indicator device 8.

Figure 6:
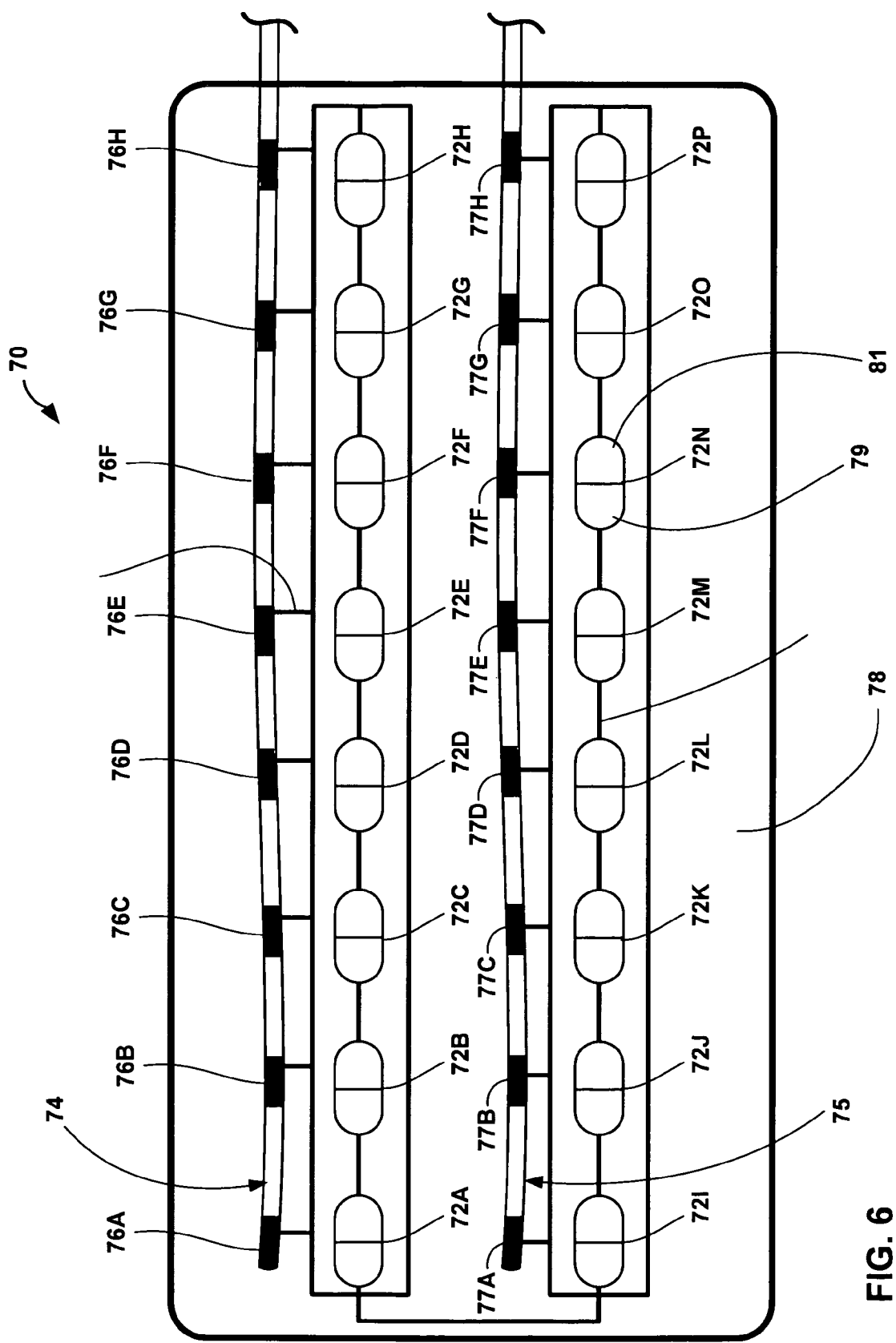
FIG. 6 is a diagram illustrating an indicator device coupled to electrodes on a lead in accordance with another embodiment of the invention.

FIG. 6 is a diagram illustrating an indicator device 70 including an array of indicators 72A-P (collectively "indicators 72) that indicate stimulation parameters for stimulation therapy delivered by electrodes 76A-H (collectively electrodes 76) on lead 74 and electrodes 77A-H (collectively electrodes 77") on lead 75. Indicator device 70 functions in a manner similar to indicator device 8, but is designed to directly receive electrodes at a distal end of one or more implantable leads. In this sense, indicator device 70 provides a built-in lead adapter that couples the electrodes to respective indicators. As shown in FIG. 6, indicators 72 are electrically coupled to a corresponding one of electrodes 76 and 77. In general, leads 74 and 75 may be coupled to a pulse generator (not shown in FIG. 6). Electrodes 76 and 77 may be coupled directly to the pulse generator via conductors within leads 74, 75 and contacts formed at the proximal ends of the leads.

Indicators 72 are electrically connected to electrodes 76 and 77 at the distal ends of leads 74 and 75, respectively. In the illustrated example, indicators 72 and electrodes 76 and 77 may be contained within an insulative carrier 78. Insulative carrier 78 may be fabricated from materials such as plastic, silicone, or other insulative materials sufficient to electrically insulate electrodes 76 and 77 and allow easy visibility of indicator lights 72. Indicator device 70 may be fabricated by placing the distal ends of leads 74, 75 such that electrodes 76, 77 reside adjacent respective indicators 72. In the example of FIG. 6, indicator device 8 permits the use of implantable leads 74, 75 to couple the output terminals of pulse generator 6 to indicators 72.

Indicator lights 72 provide a user with a clear representation of stimulation parameters for stimulation therapy generated by the pulse generator because indicator lights 72 are arranged in a pattern consistent with electrodes 76 and 77 on leads 74, 75 and simultaneously indicate stimulation parameters for stimulation therapy generated by the pulse generator in real-time. Consistent with other embodiments described herein, each indicator 72 may include a pair of LEDs 79, 81, e.g., with opposite polarities and different colors. Indicators 72 may be mounted on small circuit boards with accompanying resistors and traces or simply mounted on insulative substrates with jumper connections between LEDs and resistors.

Electrical connections can be made by soldering, welding or otherwise electrically coupling each electrode 76, 77 to a respective indicator 72. Then, the assembly can be encased in insulative carrier 78, as described above.

Circuitry associated with indicators 72 may be arranged substantially as shown in the circuit diagram of FIG. 3. For example, indicators 72 may be coupled in parallel between electrodes 76 or 77, which are coupled via internal conductors to respective output terminals on the pulse generator. In addition, series and parallel resistors may be added to indicators 72 as shown in FIG. 3. Indicators 72 are physically arranged adjacent to respective electrodes 76 or 77 carried by implantable leads 74 or 75. In this manner, indicators 72 permit visualization of the stimulation energy delivered to the electrodes 76, 77.

Figure 7:
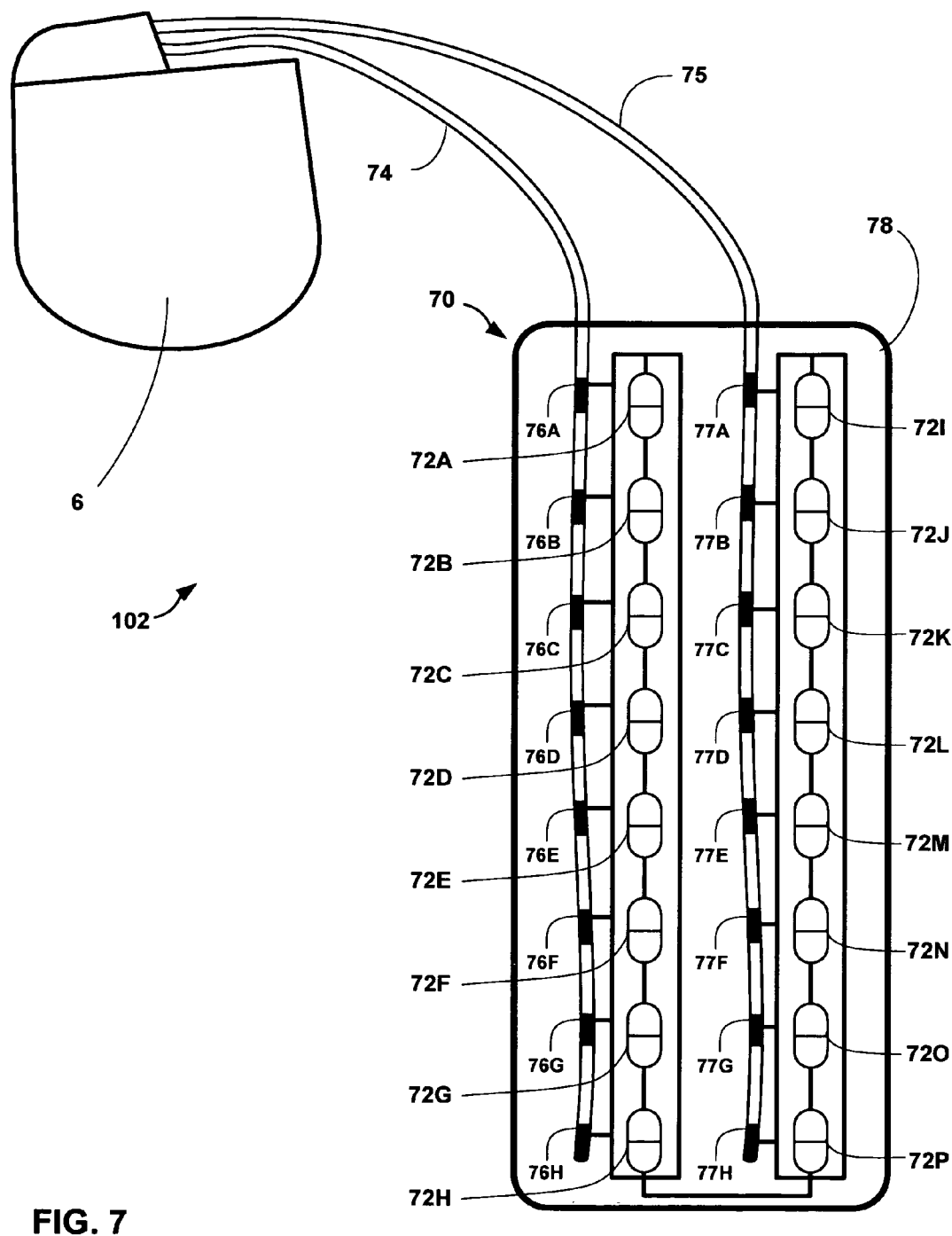
FIG. 7 is a diagram illustrating an indicator device coupled to a pair of leads extending from a pulse generator.

FIG. 7 is a diagram illustrating a system 102 that includes indicator device 70 of FIG. 6 and a pulse generator 6. As shown in FIG. 7, proximal ends of leads 74, 75 are coupled to output terminals via a connector block in pulse generator 6. Again, pulse generator may be an external pulse generator or an implantable pulse generator. In the example of FIG. 7, pulse generator is implantable. Distal ends of leads 76, 77 are mounted in indicator device 70 such that electrodes 76, 77 are arranged adjacent respective indicators 72. Distal ends of leads 76, 77 may be permanently mounted in indicator device 78 such that leads 74, 75 are permanently attached to indicator device 78. Proximal ends of leads 74, 75 can then be selectively inserted into connector blocks or lead adapters for connection to various pulse generators, as desired.

Figure 8:
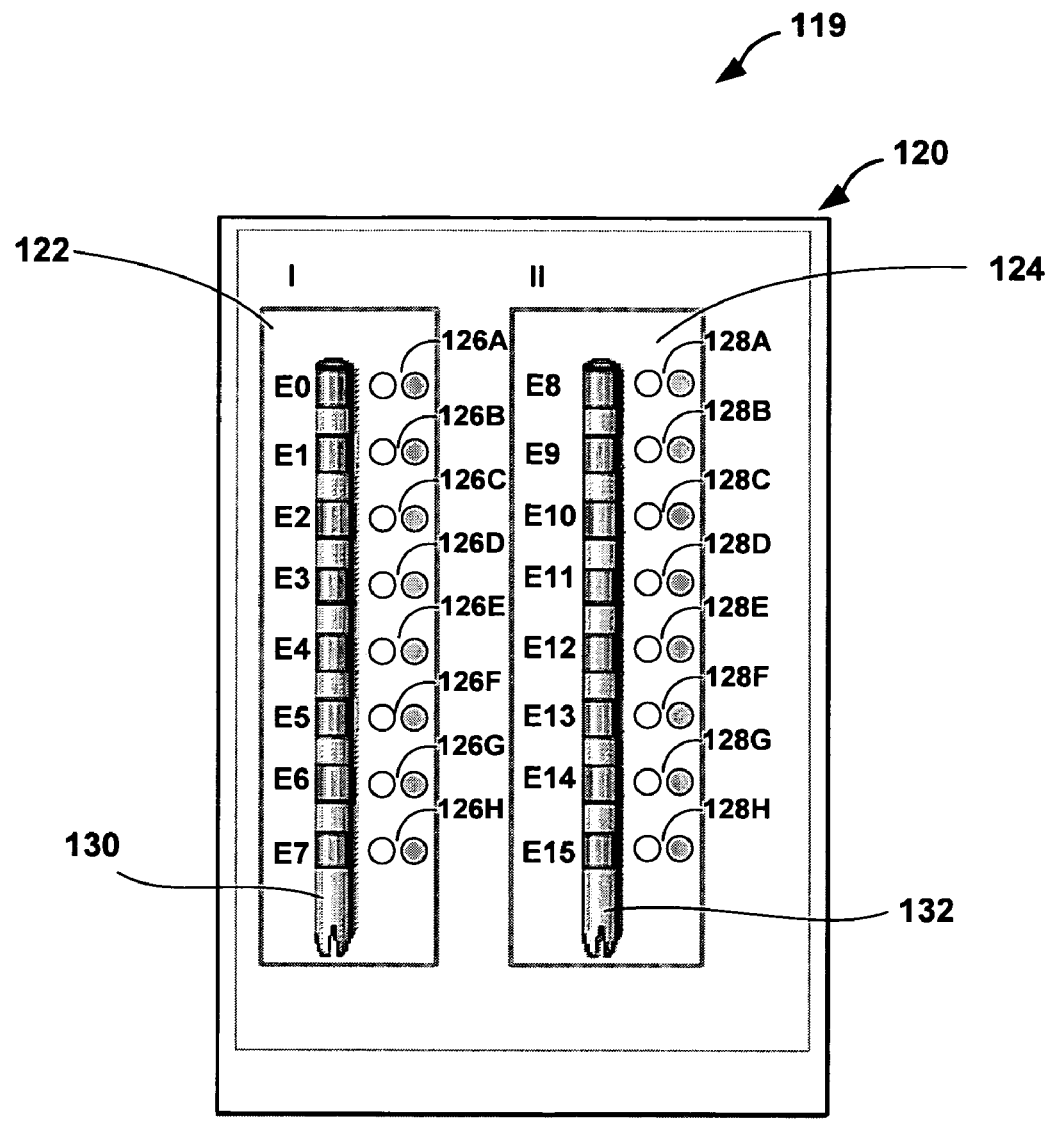
FIG. 8 is a diagram illustrating an indicator device incorporating a pixelized display for graphically representing electrical stimulation pulse parameters.

FIG. 8 is a diagram illustrating an example graphical user interface (GUI) 120 that may be provided by an indicator device 119 to indicate stimulation parameters for stimulation therapy generated by pulse generator 52. GUI 120 may be presented via a pixelized display on indicator device 119. Hence, GUI 120 represents an alternative to the use of LED's or other physically discrete indicator devices to present stimulation parameters. In the example of FIG. 8, the front face of indicator device 119 may comprise a pixelized display, such as a liquid crystal display (LCD), suitable for presenting GUI 120. The configuration of GUI 120 is merely exemplary and is provided for purposes of illustration.

GUI 120 may be designed to display stimulation parameters in a manner similar to indicator lights. For example, indicators are graphically represented to simulate emission of pulses of light with period and duration in proportion to the pulse rate and pulse width of stimulation therapy generated by the pulse generator and with intensity in proportion to the current or voltage amplitude of stimulation therapy generated by the pulse generator. Accordingly, display fields 122 and 124 each include a visual representation of an eight electrode lead 130 and 132 and an array of indicators 126A-H (collectively "indicators 126") and indicators 128A-H (collectively "indicators 128") that blink in a similar fashion as indicator lights 62.

Figure 9:
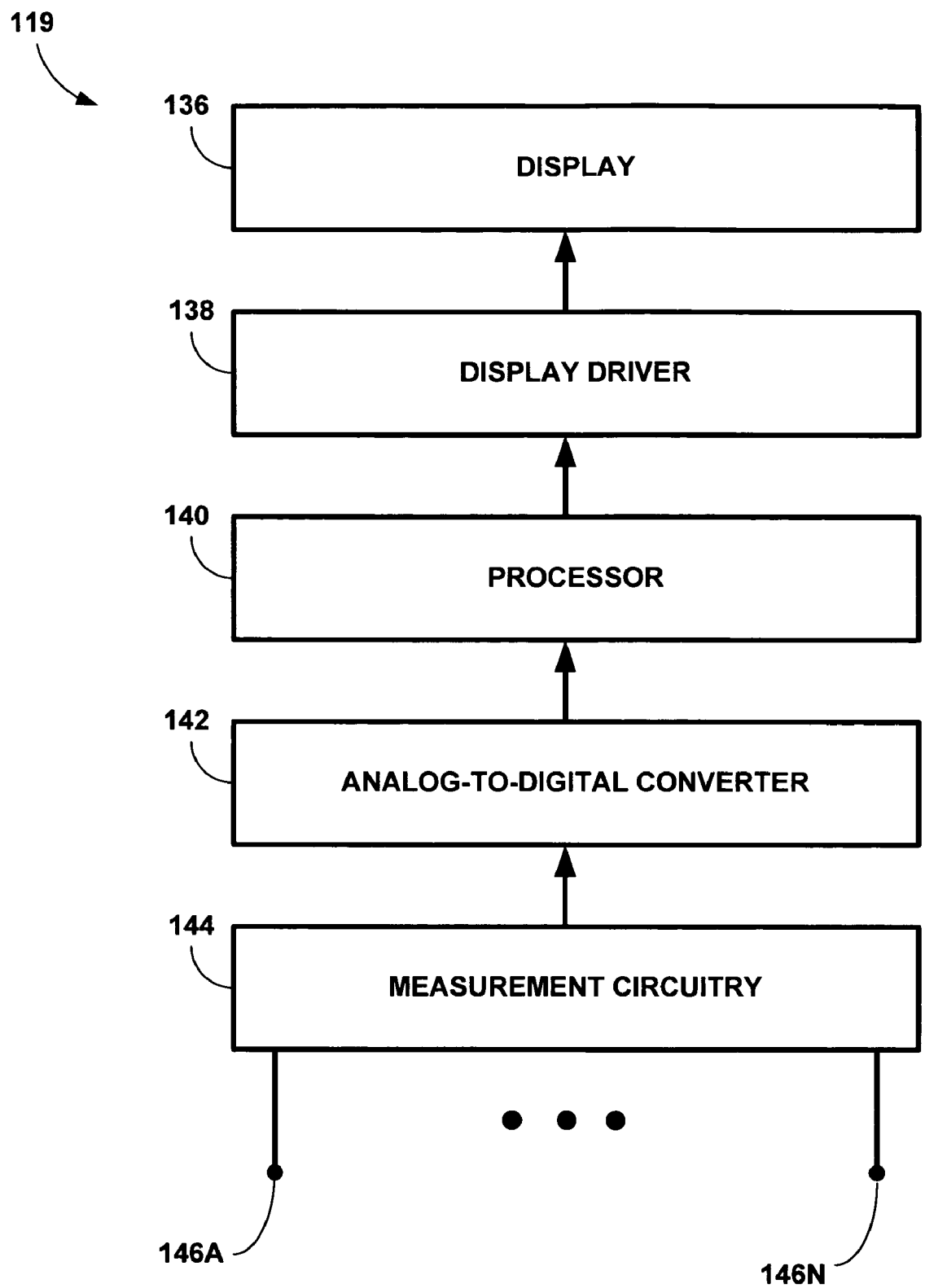
FIG. 9 is a block diagram illustrating exemplary components of the indicator device of FIG. 8.

As shown in FIG. 9, the electrodes of "virtual" lead 130 are designated E0-E7 and the electrodes of "virtual lead" 132 are designated E8-E15. Each of indicators 126 and 128 includes a pair of opposite polarity indicator lights. Each pair of opposite polarity lights includes one polarity light that activates, i.e., blinks, when the corresponding channel of pulse generator 52 acts as an anode and another polarity light that activates when the channel acts as a cathode. The two polarity lights included in each of indicator lights 126 and 128 may be colored different to indicate when the corresponding channel acts as an anode or cathode.

In various embodiments described herein, stimulation pulses are applied directly to indicators to drive pertinent indicator lights. In the example of FIG. 8, however, indicators 126, 128 are graphically depicted by a pixelized display. For this reason, indicator device 119 further includes appropriate circuitry and processing electronics to measure one or more parameters associated with stimulation pulses and drive GUI 120 to present the appropriate view of indicators 126, 128. For example, indicator device 119 may include measurement electronics to measure voltage or current amplitude, pulse rate, and pulse width and determine polarity for stimulation pulses delivered at the output terminals of the pulse generator.

FIG. 9 is a block diagram illustrating exemplary components of the indicator device 119 of FIG. 8. As shown in FIG. 9, indicator device 119 includes a graphical display 136 to present GUI 120, display driver electronics 138 to drive the display, a processor 140, analog-to-digital converter (ADC) 142, and measurement circuitry 144. Measurement circuitry 144 measures parameters associated with stimulation pulses delivered via output terminals 146A-146N of a pulse generator. The parameters may include voltage or current amplitude, pulse rate, pulse width, and polarity. ADC 142 converts the measured parameters to digital values or processing by processor 140. Processor 140 generates display control values based on the digital values and applies them to display driver 138. Display driver 138 then drives display 136 to present the measured values via GUI 120 on display 136.

Measurement circuitry 144 may include appropriate electronic components such as resistors, diodes, comparators, and sample and hold circuitry sufficient to capture the stimulation pulse parameters discussed above. ADC 142, processor 140 and display deriver 138 may be formed by integrated circuitry. In particular, processor 140 may be a microprocessor, digital signal processor (DSP), application specific integrated circuit (ASIC), field programmable gate array (FPGA), or any combination of such components.

Various embodiments of the invention, as broadly embodied and described herein, may be applied to visualize stimulation pulse parameters associated with a wide variety of stimulation therapies, including neurostimulation therapy to treat symptoms or conditions such as chronic pain, tremor, Parkinson's disease, epilepsy, incontinence, sexual dysfunction, obesity, or gastroparesis. Accordingly, the invention may be employed in conjunction with pulse generators designed for spinal cord stimulation, pelvic floor stimulation, peripheral nerve stimulation, or deep brain stimulation.

Various embodiments of the invention have been described. These and other embodiments are within the scope of the following claims.

The invention claimed is:

1. A method comprising:
   receiving electrical stimulation pulses applied by a pulse generator across a set of output terminals; and
   indicating one or more parameters associated with the electrical stimulation pulses via an array of visual indicators, wherein each of the indicators corresponds to one of the output terminals, the output terminals are coupled to drive the indicators, and the indicators are physically arranged to represent relative positions of electrodes carried by one or more implantable leads.

2. The method of claim 1, wherein the indicators are arranged as a first column of indicators representing electrodes carried by a first implantable lead, and a second column of indicators representing electrodes carried by a second implantable lead.

3. The method of claim 1, wherein the parameters include at least one of electrical voltage, electrical current, electrical energy, pulse width, pulse rate, and polarity.

4. The method of claim 1, further comprising indicating polarities of the stimulation pulses applied to the output terminals.

5. The method of claim 1, wherein the indicators include indicator lights, the method further comprising activating the indicator lights as a function of the stimulation pulses applied across the corresponding terminals.

6. The method of claim 5, further comprising activating each of the corresponding indicator lights with an intensity proportional to one or more of the parameters.

7. The method of claim 5, wherein each of the indicators includes a first indicator light and a second indicator light, the method further comprising activating the first indicator light to indicate positive polarity and activating the second indicator light to indicate negative polarity.

8. The method of claim 7, wherein the first indicator light includes a first light emitting diode and the second indicator light includes a second light emitting diode, the first and second light emitting diodes being coupled in parallel with opposite polarities such that the first light emitting diode activates in response to a positive voltage and the second light emitting diode activates in response to a negative voltage.

9. The method of claim 1, wherein the indicators are presented by a pixelized display device.

10. The method of claim 1, wherein the electrical stimulation pulses are generated at a substantially slower pulse rate and a substantially longer pulse width than electrical stimulation pulses typically selected to provide stimulation therapy to a patient, thereby facilitating visual indication of the electrical parameters.

11. The method of claim 1, wherein the electrical stimulation pulses are not applied to a patient.

12. A device comprising:
    an array of visual indicators that indicate one or more parameters associated with electrical stimulation pulses generated by a pulse generator across a set of output terminals; and
    an interface that electrically couples the output terminals associated with the pulse generator to drive the indicators to indicate the one or more parameters, wherein each of the indicators corresponds to one of the output terminals, and wherein the indicators are physically arranged to represent relative positions of electrodes carried by one or more implantable leads.

13. The device of claim 12, wherein the indicators are arranged as a first column of indicators representing electrodes carded by a first implantable lead, and a second column of indicators representing electrodes carried by a second implantable lead.

14. The device of claim 12, wherein the parameters include at least one of electrical voltage, electrical current, electrical energy, pulse width, pulse rate, and polarity.

15. The device of claim 12, wherein the indicators indicate polarities of the stimulation pulses applied to the output terminals.

16. The device of claim 12, wherein the indicators include indicator lights, the indicator lights being activated as a function of the stimulation pulses applied across the corresponding terminals.

17. The device of claim 16, wherein each of the corresponding indicator lights is activated with an intensity proportional to one or more of the parameters.

18. The device of claim 16, wherein each of the indicators includes a first indicator light and a second indicator light, the first indicator light being activated to indicate positive polarity and the second indicator light being activated to indicate negative polarity.

19. The device of claim 18, wherein the first indicator tight includes a first light emitting diode and the second indicator light includes a second light emitting diode, the first and second light emitting diodes being coupled in parallel with opposite polarities such that the first light emitting diode activates in response to a positive voltage and the second light emitting diode activates-in response to a negative voltage.

20. The device of claim 12, further comprising a pixelized display device, wherein the indicators are presented by the pixelized display device.

21. The device of claim 12, wherein the electrical stimulation pulses are generated at a substantially slower pulse rate and a substantially longer pulse width than electrical stimulation pulses typically selected to provide stimulation therapy to a patient, thereby facilitating visual indication of the electrical parameters.

22. The device of claim 12, wherein each of the indicators includes a first light emitting diode and a second light emitting diode coupled in parallel with opposite polarities such that the first light emitting diode activates in response to a positive voltage and the second light emitting diode activates in response to a negative voltage, and wherein each of the indicators further includes a resistor coupled between the respective first and second light emitting diodes and the corresponding output terminal, the resistor having a resistance selected to set a turn-on current for the first and second light emitting diodes.

23. The device of claim 22, wherein the interface couples at least some of the indicators in series between a first one of the output terminals and a second one of the output terminals.

24. The device of claim 12, wherein the output terminals are not coupled to the electrodes carried by the one or more implantable leads.

25. A system comprising:
a pulse generator that generates electrical stimulation pulses across a set of output terminals;
an indicator device having an array of visual indicators that indicate one or more parameters associated with the electrical stimulation pulses generated by the pulse generator; and
an interface that electrically couples the output terminals to drive the indicators to indicate the one or more parameters, wherein each of the indicators corresponds to one of the output terminals, and wherein the indicators are physically arranged to represent relative positions of electrodes carried by one or more implantable leads.

26. The system of claim 25, wherein the indicators are arranged as a first column of indicators representing electrodes carried by a first implantable lead, and a second column of indicators representing electrodes carried by a second implantable lead.

27. The system of claim 25, wherein the parameters include at least one of electrical voltage, electrical current, electrical energy, pulse width, pulse rate, and polarity.

28. The system of claim 25, wherein the indicators indicate polarities of the stimulation pulses applied to the output terminals.

29. The system of claim 25, wherein the indicators include indicator lights, the indicator Lights being activated as a function of the stimulation pulses applied across the corresponding terminals.

30. The system of claim 29, wherein each of the corresponding indicator lights is activated with an intensity proportional to one or more of the parameters.

31. The system of claim 29. wherein each of the indicators includes a first indicator light and a second indicator light, the first indicator light being activated to indicate positive polarity and the second indicator light being activated to indicate negative polarity.

32. The system of claim 31, wherein the first indicator light includes a first light emitting diode and the second indicator Light includes a second light emitting diode, the first and second light emitting diodes being coupled in parallel with opposite polarities such that the first light emitting diode activates in response to a positive voltage and the second light emitting diode activates in response to a negative voltage.

33. The system of claim 25, wherein the indicator device includes a pixelized display device, wherein the indicators are presented by the pixelized display device.

34. The system of claim 25, wherein the pulse generator generates the electrical stimulation pulses at a substantially slower pulse rate and a substantially longer pulse width tan electrical stimulation pulses typically selected to provide stimulation therapy to a patient, thereby facilitating visual indication of the electrical parameters.

35. The system of claim 25, wherein the pulse generator includes a pulse rate selector that receives input from a user to select the pulse rate at which the pulse generator generates electrical stimulation and selects the pulse rate based on input received from the user.

36. The system of claim 25, further comprising an external programmer to control the pulse generator.

37. The system of claim 25, wherein the interface that electrically couples the indicators to the output terminals includes at least one medical lead carrying electrodes, wherein the lead includes conductors that couple the output terminals to the electrodes, and the electrodes are electrically coupled to the indicators.

38. The system of claim 25, wherein each of the indicators includes a first light emitting diode and a second light emitting diode coupled in parallel wit opposite polarities such that the first light emitting diode activates in response to a positive voltage and the second light emitting diode activates in response to a negative voltage, and wherein each of the indicators further includes a resistor coupled between the respective first and second light emitting diodes and the corresponding output terminal, the resistor having a resistance selected to set a turn-on current for the first and second light emitting diodes.

39. The system of claim 38, wherein the interface couples at least some of the indicators in series between a first one of the output terminals and a second one of the output terminals.

40. The system of claim 25, wherein the output terminals are not coupled to the electrodes carried by the one or more implantable leads.

\* \* \* \* \*

UNITED STATES PATENT AND TRADEMARK OFFICE
CERTIFICATE OF CORRECTION

| | | |
|---|---|---|
| PATENT NO. | : 7,551,960 B2 | Page 1 of 1 |
| APPLICATION NO. | : 11/222501 | |
| DATED | : June 23, 2009 | |
| INVENTOR(S) | : Forsberg et al. | |

It is certified that error appears in the above-identified patent and that said Letters Patent is hereby corrected as shown below:

Col. 14, Line 63: "indicator tight includes" should read --indicator light includes--

Col. 16, Line 22: "width tan electrical" should read --width than electrical--

Col. 16, Line 40: "parallel wit opposite" should read --parallel width opposite--

Signed and Sealed this
Third Day of May, 2011

David J. Kappos
*Director of the United States Patent and Trademark Office*